United States Patent
Hultmark et al.

(10) Patent No.: US 11,054,290 B2
(45) Date of Patent: Jul. 6, 2021

(54) ELASTIC FILAMENT VELOCITY SENSOR

(71) Applicant: The Trustees of Princeton University, Princeton, NJ (US)

(72) Inventors: Marcus Hultmark, Princeton, NJ (US); Clay Byers, Princeton, NJ (US); Matthew Fu, Princeton, NJ (US); Yuyang Fan, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 11 days.

(21) Appl. No.: 16/737,442

(22) Filed: Jan. 8, 2020

(65) Prior Publication Data
US 2020/0141772 A1 May 7, 2020

Related U.S. Application Data

(63) Continuation of application No. 15/759,957, filed as application No. PCT/US2016/040975 on Jul. 5, 2016, now Pat. No. 10,539,443.
(Continued)

(51) Int. Cl.
*G01F 1/28* (2006.01)
*G01F 1/698* (2006.01)
(Continued)

(52) U.S. Cl.
CPC .............. *G01F 1/28* (2013.01); *G01F 1/20* (2013.01); *G01F 1/684* (2013.01); *G01F 1/698* (2013.01);
(Continued)

(58) Field of Classification Search
CPC ... G01F 1/28; G01F 1/698; G01F 1/20; G01F 1/684; G01P 5/02; A61B 2562/0261; A61B 5/0285
(Continued)

(56) References Cited

U.S. PATENT DOCUMENTS 4,419,888 A * 12/1983 Kitamura ............... G01N 25/64
73/23.21
4,448,081 A 5/1984 Kolitsch et al.
(Continued)

FOREIGN PATENT DOCUMENTS

DE 102005051785 A1 5/2007
WO 2000/39537 A1 7/2000

OTHER PUBLICATIONS

International Search Report for PCT/US2016/040975, dated Sep. 14, 2016.
(Continued)

*Primary Examiner* — Nathaniel T Woodward
(74) *Attorney, Agent, or Firm* — Meagher Emanuel Laks Goldberg & Liao, LLP.

(57) ABSTRACT

Disclosed is an apparatus for measuring velocity of a fluid stream via deflection of a wire filament. Also disclosed is a process for measuring velocity of a fluid stream, requiring deflecting two or more wire filaments in a fluid stream, measuring two or more resistances, and equating the velocity of the fluid stream to the result of a function of the two or more resistances. In both the apparatus and method, one wire filament must have a length dimension longer than at least one of a dimension of the wire filament in the primary sensing or transverse direction, as well as a dimension of the wire filament in the primary sensing and/or transverse direction less than $$\frac{50\mu}{U\rho}$$

throughout a predetermined operating range.

20 Claims, 14 Drawing Sheets

Related U.S. Application Data

(60) Provisional application No. 62/296,339, filed on Feb. 17, 2016, provisional application No. 62/271,855, filed on Dec. 28, 2015.

(51) Int. Cl.
  *G01F 1/20* (2006.01)
  *G01F 1/684* (2006.01)
  *G01P 5/02* (2006.01)
  *A61B 5/0285* (2006.01)

(52) U.S. Cl.
  CPC .............. *G01P 5/02* (2013.01); *A61B 5/0285* (2013.01); *A61B 2562/0261* (2013.01)

(58) Field of Classification Search
  USPC ....................................................... 73/861.74
  See application file for complete search history.

(56) References Cited

U.S. PATENT DOCUMENTS

| | | | |
|---|---|---|---|
| 4,793,181 A * | 12/1988 | Djorup | G01N 27/121 73/29.02 |
| 5,721,492 A | 2/1998 | Saenger | |
| 9,500,615 B2 * | 11/2016 | Hultmark | G01N 27/121 |
| 2004/0040386 A1 | 3/2004 | Higgins | |
| 2009/0233057 A1 | 9/2009 | Aksay et al. | |
| 2015/0075280 A1 | 3/2015 | Hultmark et al. | |

OTHER PUBLICATIONS

Written Opinion for PCT/US2016/040975, dated Sep. 14, 2016.
G. Arwatz et al: "Development and characterization of a nano-scale temperature sensor (T-NSTAP) for turbulent temperature measurements", Meas. Sci. Technol. 26 (2015).
C. Bahri et al.: "Self-similarity of passive scalar flow in grid turbulence with a mean cross-stream gradient", J. Fluid Mech. vol. 780, pp. 215-225. (2015).
M. Hultmark et al.: "Turbulent Pipe Flow at Extreme Reynolds Numbers", Physical Review Letters, PRL 108, 094501 (2012).
William K. George and Luciano Castillo: "The Zero Pressure-Gradient Turbulent Boundary Layer", Applied Mechanics Reviews, vol. 50, No. 12, pp. 689-729, Dec 1, 1997.
H. H. Fernholz and P. J. Finley: "The Incompressible Zero-Pressure-Gradient Turbulent Boundary Layer: An Assessment of the Data", Prog. Aerospace Sci. vol. 32, pp. 245-311, 1996.
M. K. Fu et al.: "Elastic filament velocimetry (EFV)", Meas. Sci. Technol. 28 (2017) 025301 (12pp), 2017.
European Search Report issued in corresponding EP 16882218.7 dated Jul. 10, 2019.
Hristoforou et al., "New flowmeters based on amorphous magnetic wires", Sensors and Actuators A 59 (1997) 94-96.

* cited by examiner

ELASTIC FILAMENT VELOCITY SENSOR

CROSS-REFERENCE TO RELATED APPLICATIONS

This application claims benefit of U.S. Provisional Application Nos. 62/271,855, filed Dec. 28, 2015, and 62/296,339 filed Feb. 17, 2016, which are hereby incorporated in its entirety by reference.

BACKGROUND OF THE INVENTION

Many processes and/or devices use or manipulate moving fluids. From vehicles (e.g., cars, planes, boats, or submarines), to homes (e.g., heating and ventilating systems, water pipes), to many of the modern industrial processes, there is a reliance on the use and flow of various gasses. Typically, for these processes and/or devices, it is important that the velocity of the fluid be accurately determined. Accordingly, various techniques to determine the velocity of a fluid have been developed.

The idea of using calibrated strain gauges to measure fluid velocity is not a new idea. Most of these currently known ideas involve utilizing calibrated cantilevers or plates embedded with strain gauges on one or more surfaces. The bending and deflection of the entire member is then calibrated to the fluid velocity. However, these devices are complicated and expensive. A simpler and less expensive technique for utilizing the strain gauge effect to measure fluid velocity would be beneficial.

BRIEF SUMMARY OF THE INVENTION

The present invention is directed towards a system and method for measuring velocity by deflecting an appropriately configured wire filament. These systems and methods utilize wires having at least one dimension—including but not limited to dimensions such as width, thickness and diameter—less man $$\frac{50\mu}{U\rho}$$

throughout a predetermined operating range, where $\mu$ is viscosity of the fluid stream, $\rho$ is density of the fluid stream, and U is velocity of the fluid stream relative to the at least one wire filament. In one embodiment, two dimensions are less than $$\frac{50\mu}{U\rho}$$

throughout a predetermined operating range

Among the many different possibilities contemplated, the wire filament may also be supported at both ends. It is also contemplated that wire filament is freestanding. It is further contemplated that the length of the wire filament is between and including 10 and 100,000 times that of both the primary sensing and transverse dimensions. It is still further contemplated that the wire filament comprises material with a Young's modulus between and including 0.001 and 500 GPa, and a yield strength between and including 30 and 3,000 MPa.

It is often desirable for wire filaments to be comprised of materials having low thermal coefficients of resistance ("TCR"). In some embodiments, the wire filament is comprised of materials having TCR values between $1\times10^{-2}$ and $1\times10^{-8}$ 1/° C. In a preferred embodiment, the TCR values were between $1\times10^{-4}$ and $1\times10^{-8}$ 1/° C. Further, it is often desirable for wire filaments to have moderate to high gain factors. For example, in some embodiments, the wire filament has a gain factor between 2 and 1000. In a preferred embodiment, the gain factors were between 2 and 6.1.

It is still further contemplated that a dimension of the wire filament in the primary sensing direction is less than $$L\left(\frac{\mu U}{Ew}\right)^{\frac{1}{4}},$$

where $\mu$ is viscosity of the fluid stream, E is the Young's modulus of the wire filament, w is the dimension in the transverse direction, L is the filament length, and U is velocity of the fluid stream relative to the wire. It is contemplated that this wire filament comprises a material that experiences a change in its resistance when deformed, and may comprise various materials, including a pure metal or a metal alloy, an electrically conductive polymer, or a piezoresistive material, and may further include at least one additional material.

It is further contemplated that the sensor could comprise two or more wire filaments, and that the first wire filament could have a different sensitivity to at least one of velocity or temperature than the second wire filament.

It is also contemplated that the sensor could be configured appropriately for a variety of environments, including measuring flow rates in fluid delivery systems, pressure differences in ventilation systems, or air or water speed of vehicles.

Various systems are also contemplated, which comprise a sensor and a circuit configured to measure a voltage or resistance of the wire filament. It is also contemplated that such a sensor system could comprise a circuit configured to automatically adjust the output for temperature or current changes. Such a system is further contemplated to comprise a processor for receiving a signal comprising the voltage or resistance of the wire filament and output a signal comprising a calculated fluid stream velocity. It is contemplated that the sensor system could also comprise a wireless transceiver capable of transmitting a signal comprising voltage of the wire filament, resistance of the wire filament, and/or a calculated fluid stream velocity. It is contemplated that a sensor housing may be required to protect at least the circuit, if not a majority of the device.

DETAILED DESCRIPTION OF THE INVENTION

Figure 1:
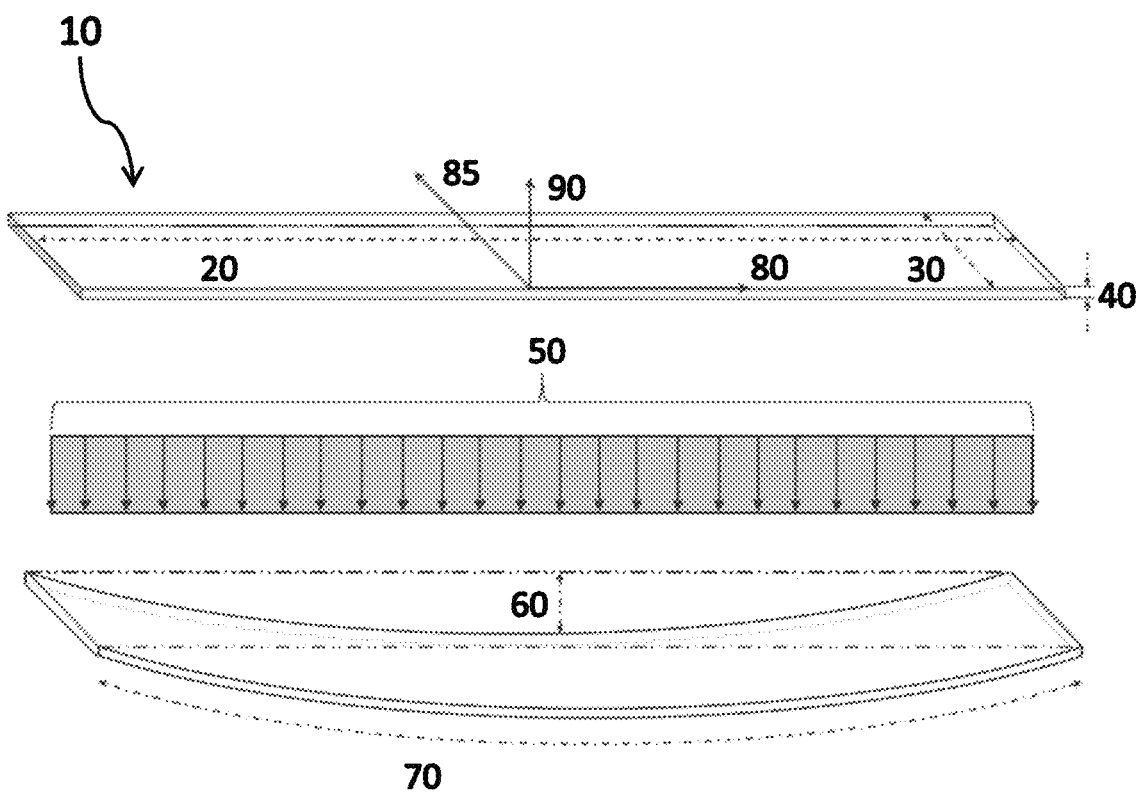
FIG. 1 is an illustration of one embodiment of a wire of the present invention.

The device described herein is far simpler in design and operation than those previously considered, at least in part because the calibrated member and strain gauge are one and the same. This design allows us to eliminate the most complicated and expensive aspects of existing sensing methods, resulting in simpler design and operation.

Disclosed is a sensor for measuring the velocity of a passing fluid through the use of a freestanding, electrically conductive filament, preferably a nano-filament. The filament should be configured such that it is capable of being deflected by a flowing fluid to be measured. The drag force from the passing flow would then deflect the filament, inducing an axial strain. The combination of the elongation and piezoresistive effects relates the axial strain to a change in electrical resistance across the filament, i.e. a strain gauge effect. Generally, because the fluid drag on the filament increases with fluid velocity, the passing fluid velocity can be correlated with a measured resistance change.

One of the novel aspects of the sensor lies in simplicity of the form and function. In one embodiment, the freestanding wire filament is exposed to fluid flow, causing it to deform and elongate. The geometric simplicity and large aspect ratios enables semi-analytic treatment of the fluid loading and elastic deformation, while the small thickness enables a high degree of sensitivity.

To design a wire filament with optimal sensitivity for a given velocity range, relationships must be established between axial strain and fluid velocity. Consider the embodiment of a wire illustrated in FIG. 1. A wire (10) shown with global cartesian coordinates $\hat{x}$ (80), $\hat{y}$ (85) and $\hat{z}$ (90) has a rectangular cross section where the span (20), $L_o$, is much greater than the base (30), b, and thickness (40), h, the latter of which shall be considered the nanoscale dimension. Under uniform loading (50), $q\hat{z}$, along the thickness-wise dimensions, the wire will experience a maximal deflection (60) δ to an elongated length (70), L, yielding an overall elongation of $L-L_o$.

Figure 14:
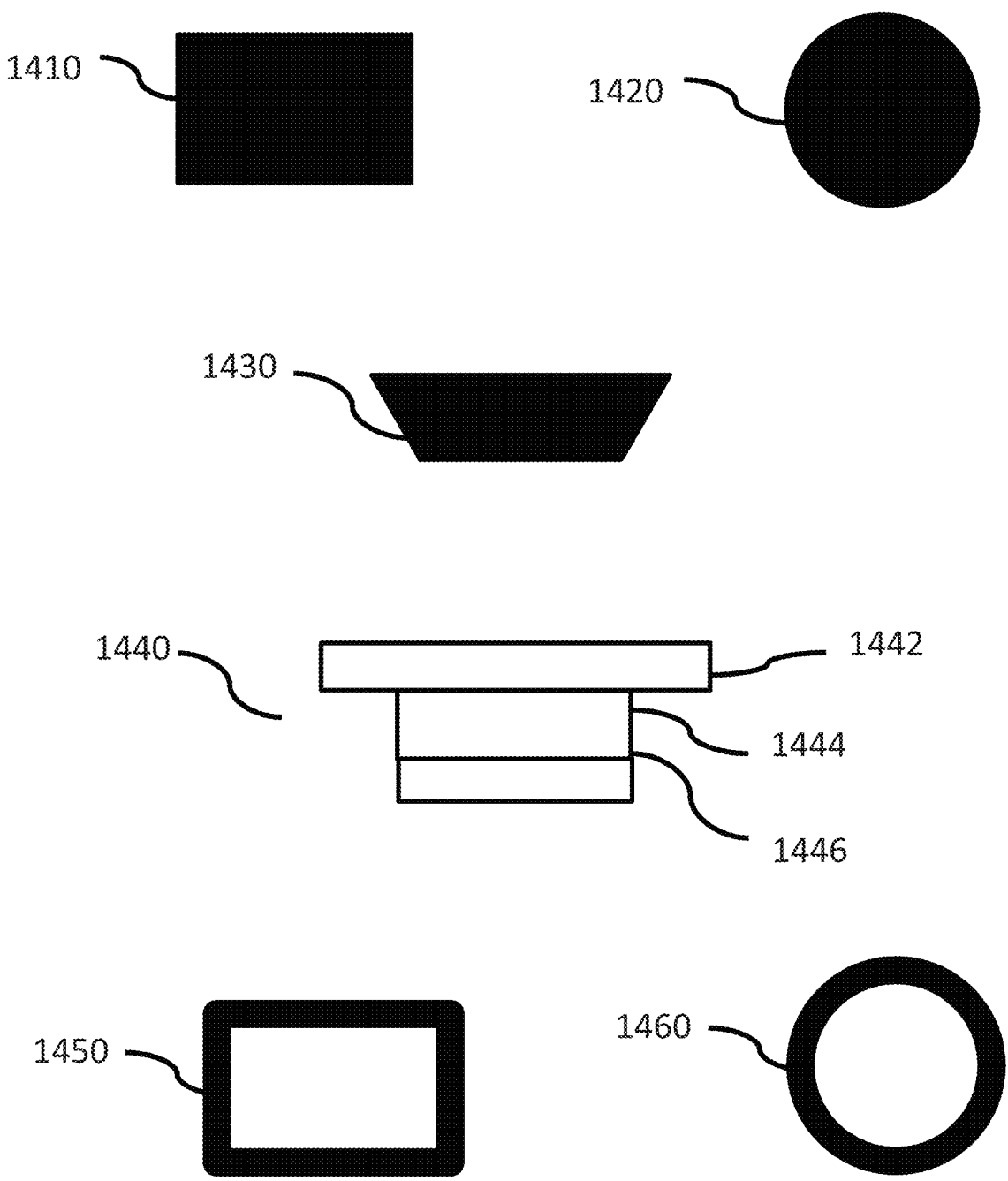
FIG. 14 is an illustration of cross-sections of various embodiments of wire filaments.

While the wire is shown in FIG. 1 as having a rectangular cross-section, other cross-sections and constructions are acceptable. Some variations are shown in FIG. 14. These variations include, but are not limited to, rectangular (1610), circular (1620), and trapezoidal (1430) cross sections. Another wire filament option could use multiple layers (1440). FIG. 14 shows one option having three layers (1442, 1444, 1446), each of which may be constructed of different materials, and each layer may have a different cross-section. FIG. 14 shows one embodiment where a first layer (1442) has a different width than a second layer (1444) or third layer (1446), and the second layer has a different thickness than the other two layers. Other non-limiting options include hollow cross-sections (1450, 1460). In a preferred embodiment, the span or length of the at least one wire filament is between and including 10 and 100,000 times that of both the base and thickness or the transverse and primary sensing dimensions. More preferably, the span or length is between and including 100 and 10,000 times that of both the base and thickness or the primary sensing and traverse dimensions. Further, although shown in FIG. 1 as a freestanding wire, the wire filament may also be supported at both ends. Additional wires also may or may not be freestanding. For example, a temperature measurement wire, or a resistance compensation wire may be freestanding, but also function when not freestanding.

When considering a nanoscale dimension, it is preferable to choose a thickness or primary sensing direction several orders of magnitude smaller than the length of the wire to exhibit negligible flexural rigidity to loading along that dimension. In doing so, the result is that the governing force balance is dominated by the internal tension rather than classic Euler-Bernoulli bending theory.

In one embodiment, the dimension of the at least one wire filament in the primary sensing direction is less than $$L\left(\frac{\mu U}{Ew}\right)^{\frac{1}{4}},$$

where μ is viscosity of the fluid stream, E is the Young's modulus of the wire filament, w is the dimension in the transverse direction, L is the filament length of the sensor of claim 1, and U is velocity of the fluid stream relative to the wire.

Consequently, any component of fluid flow aligned with the nanoscale dimension will elastically elongate the wire until the deformation and internal stress is sufficient to balance the fluid drag force. This net elongation can be measured as a resistance change across the length of the wire filament, an effect that is amplified if the material is piezoresistive. The deformation, and the corresponding elongation, from an external loading can be determined using beam theory. The steady-state deflection of the wire filament of uniform cross section under uniform loading with pinned ends is governed by $$EI\frac{d^4w}{dx^4} - N\frac{d^2w}{dx^2} = q \qquad \text{(Eq. 1)}$$

where E is the elastic modulus of the material, I is the second moment of area and given as $$I = \frac{bh^3}{12}$$

for a wire with rectangular cross section, w is the deflection from the neutral axis, N is the axial tension in the beam arising from elastic deformation. Furthermore, the wire filament is assumed to have a large radius of curvature, R, where $R \gg L_o$. This assumption, the small angle approximation, is called upon repeatedly in this analysis and its validity for this sensor was evaluated using laser scanning confocal microscopy.

The small angle approximation allows treatment of the wire filament coordinate system as aligned with the global Cartesian system in FIG. 1. This assumption enables significant simplification of the governing dynamics and can be validated with consideration of the particular flow and wire parameters. In this case, N in equation 1 can be treated as constant through the span of the wire.

Scaling of this equation in terms of dimensionless parameters and dimensional coefficients reveals the relative importance of the Euler-Bernoulli term to the internal tension. The given parameters in equation 1 can be scaled as $w=\delta\bar{w}, x=L_o\bar{x}$, where overlined parameters are dimensionless and order unity and are preceded by an appropriate dimensional constant. Note that though $\delta$ is the midpoint deflection, the scale relative to the other parameters is not yet known. Assume that the N is tension arising solely from the net axial strain in the wire (i.e. neglecting pretension), and A is the cross sectional area and given by A=bh, it can be scaled in the follow manner as $N=EA\delta^2 L_o^{-2}\underline{N}$. Expressing equation 1 in terms of these dimensionless parameters yields $$0 = -\frac{Ebh\delta^3}{QL^4}\left(\frac{h^2}{12\delta^2}\left[\frac{\partial^4 \bar{w}}{\partial \bar{x}^4}\right] - \left[\underline{N}\frac{\partial^2 \bar{w}}{\partial \bar{x}^2}\right]\right) + [\bar{q}] \qquad \text{(Eq. 2)}$$

Terms inside of the square brackets are comprised solely of dimensionless scaling functions and variables and therefore order unity. Each of these terms is preceded by a grouping of scaling parameters that indicates the relative importance of each dimensionless scaling function to force balance. When the scale of the deflection, $\delta$, is such that $\delta \gg h$, the first bracketed term is negligible to the overall force balance $$\delta \sim (QL^4(Ebh)^{-1})^{\frac{1}{3}}.$$

If an external loading is considered coincident with h, the governing equation for the deflection across the wire in time, t is given by:

$$\rho_s A\frac{\partial^2 w}{\partial t^2} - \left(\rho_s I + \frac{\rho_s EI}{\kappa G}\right)\frac{\partial^4 w}{\partial x^2 \partial t^2} + \frac{\rho_s^2 I}{\kappa G}\frac{\partial^4 w}{\partial t^4} + \frac{\rho_s I\eta}{\kappa AG}\frac{\partial^3 w}{\partial t^3} +$$
$$\frac{EI}{\kappa AG}\frac{\partial^2 w}{\partial x^2}\left(\eta\frac{\partial w}{\partial t}\right) + \eta\frac{\partial w}{\partial t} = -EI\frac{\partial^4 w}{\partial x^4} + N\frac{\partial^2 w}{\partial x^2} + q - \frac{EI}{\kappa AG}\frac{\partial^2 q}{\partial x^2}$$

For this wire configuration $\rho_s$ is the density of the nanowire, A is the cross sectional area of the wire (A=bh), I is the second moment of area (I=bh³/12), w is the deflection from the neutral axis, x denotes the spanwise axis along the wire, $\kappa$ is the Timoshenko shear coefficient, G is the shear modulus, E is the elastic modulus, $\eta$ is linear damping coefficient from the surrounding fluid, q is the loading per unit span and N the axial tension in the wire from elastic deformation. It is assumed that the deflections are significantly smaller than the span of the wire to ensure that the deformation of the wire is elastic and well below the yield point of at least some, and preferably all, of the materials comprising the wire filament. Under this assumption, N can be treated as constant across the length of the wire.

Using knowledge of the geometry, fluid flow and material properties, the governing Timoshenko beam equation can be expressed in terms of nondimensional quantities and derivatives, scaled by dimensional coefficients. This can be scaled as $w=\delta\bar{w}, t=\omega^{-1}\bar{t}, x=L\bar{x}, q=Q\bar{q}$. Note that $\delta$ and $\omega$ are yet to known, but prescribed such that the dimensionless terms are order unity. Q is the scale of the applied loading. The size of Q will typically be known within a given range for a desired application. If it is first assumed that the N is tension arising from the net axial strain in the wire, it can be scaled in the follow manner with $N=EA\delta^2 L^{-2}\bar{N}$.

$$\rho_s A\delta\omega^2\left[\frac{\partial^2 \bar{w}}{\partial \bar{t}^2}\right] - \frac{\rho_s I\delta\omega^2}{L^2}\left(1+\frac{E}{\kappa G}\right)\left[\frac{\partial^4 \bar{w}}{\partial \bar{x}^2 \partial \bar{t}^2}\right] + \frac{\rho_s^2 I\delta\omega^4}{\kappa G}\left[\frac{\partial^4 \bar{w}}{\partial \bar{t}^4}\right] +$$
$$\frac{\rho_s I\mu\delta\omega^3}{\kappa AG}\left[\frac{\partial^3 \bar{w}}{\partial \bar{t}^3}\right] + \frac{EI\eta\delta^2\omega}{\kappa AGL^2}\left[\frac{\partial^2 \bar{w}}{\partial \bar{x}^2}\left(\frac{\partial \bar{w}}{\partial \bar{t}}\right)\right] + \eta\delta\omega\left[\frac{\partial \bar{w}}{\partial \bar{t}}\right] =$$
$$-\frac{EI\delta}{L^4}\left[\frac{\partial^4 \bar{w}}{\partial \bar{x}^4}\right] + \frac{EA\delta^3}{L^4}\left[\bar{N}\frac{\partial^2 \bar{w}}{\partial \bar{x}^2}\right] + Q[\bar{q}] - \frac{EIQ}{\kappa AGL^2}\left[\frac{\partial^2 \bar{q}}{\partial \bar{x}^2}\right]$$

Terms in square brackets are dimensionless and are on the order of unity and are scaled by dimensional constants. To determine the scale of the deflection, $\delta$, the steady state balance between a uniform external loading, q, and the elastic deformation of the wire can be considered. All terms with derivatives in time can be neglected and the resulting governing equation is given by the following equation:

$$0 = \frac{Ebh\delta^3}{QL^4}\left(\frac{h^2}{12\delta^2}\left[\frac{\partial^4 \bar{w}}{\partial \bar{x}^4}\right] - \left[\bar{N}\frac{\partial^2 \bar{w}}{\partial \bar{x}^2}\right]\right) + [\bar{q}]$$

From this form of the equation, the relative contributions of the flexural rigidity and internal stress towards balancing the external loading are revealed. In the case where the deflections are much larger than the thickness of the wire filament, the flexural rigidity provides negligible resistance to external loading, with most of the resistance coming from internal stress. In the case where all of the resistance is derived from the internal stress, a scale for $\delta$ can be determined as $\delta \sim (QL^4(Ebh)^{-1})^{1/3}$. It should also be noticed that if Q is insufficiently large to achieve $\delta \gg h$, the scaling analysis reverts to the classic Euler-Bernoulli result. Using these relationships, a threshold value for Q can be established to determine when the bending transitions from classic Euler-Bernoulli bending to the elongation-dominated bending where $\delta h^{-1} \gg 1 \Rightarrow Q \gg Eb(hL^{-1})^4$. Furthermore, to ensure that the beam remains in the small angle approximation regime, Q must be small enough to ensure that $\delta \ll L$. Using the same scaling, this criteria can be re-expressed as an upper bound on Q where $Q \ll Eb(hL^{-1})$.

Considering the full equation with the scale for the steady state deflection, the time scale can be determined. As the local acceleration term is assumed to be leading order, the time scale can defined as $$\omega \sim \sqrt{\frac{E\delta^2}{\rho_s L^4}} \sim \sqrt{\frac{E}{\rho_s L^4}}\left(\frac{Ebh}{qL^4}\right)^{1/3} \qquad \text{(Eq. 16)}$$

Keeping the first order terms and normalizing appropriately yields:

$$\left[\frac{\partial^2 \bar{w}}{\partial \bar{t}^2}\right] - \frac{\rho_s I\delta\omega^2}{L^2}\left(\frac{1}{AL^2} + \frac{IE}{\kappa GAL^2}\right)\left[\frac{\partial^4 \bar{w}}{\partial \bar{x}^2 \partial \bar{t}^2}\right] +$$
$$\frac{IE\delta^2}{\kappa GAL^4}\left[\frac{\partial^4 \bar{w}}{\partial \bar{t}^4}\right] + \frac{I\mu\delta}{\kappa A^2 GL^2}\sqrt{\frac{E}{\rho_s}}\left[\frac{\partial^3 \bar{w}}{\partial \bar{t}^3}\right] +$$

$$\frac{I\eta\delta}{\kappa A^2 GL^2}\sqrt{\frac{E}{\rho_s}}\left[\frac{\partial^2 \bar{w}}{\partial \bar{x}^2}\left(\frac{\partial^2 \bar{w}}{\partial \bar{t}}\right)\right] + \frac{\eta L^2}{A\delta\sqrt{\rho_s E}}\left[\frac{\partial \bar{w}}{\partial \bar{t}}\right] =$$
$$-\frac{I\delta}{\delta^2 A}\left[\frac{\partial^4 \bar{w}}{\partial \bar{x}^4}\right] + \frac{EA\delta^3}{L^4}\left[N\frac{\partial^2 \bar{w}}{\partial \bar{x}^2}\right] + |\bar{q}| - \frac{EI}{\kappa AGL^2}\left[\frac{\partial^2 \bar{q}}{\partial \bar{x}^2}\right]$$

As viscous drag is the proposed method by which the fluid flow exerts a load on the wire filament, the scaling analysis reveals the relative importance of the various viscous terms. As I is known to be very small and G is assumed to be the same order as E, it is clear that the leading order damping term is final term in the right hand side of the equation. Collecting the leading order terms, (as well as the Euler-Bernoulli bending term) and replacing the loading term with the fluid forcing discussed previously, a modified damped harmonic oscillator equation can be derived to describe the deflection of the wire filament. The full dynamical equation can be written as $$\rho_s A \frac{\partial^2 w}{\partial t^2} = -EI\frac{\partial^4 w}{\partial x^4} + N\frac{\partial^2 w}{\partial x^2} + C_D \mu\left(U - \frac{\partial w}{\partial t}\right)$$

Decomposing N into the contribution from pre-stress and the deflection induced stress, the above equation can be re-expressed as $$\rho_s A \frac{\partial^2 w}{\partial t^2} = \qquad\qquad\text{(Eq. 17)}$$
$$-EI\frac{\partial^4 w}{\partial x^4} - \frac{EA}{L_o}\left(-L_o + \int_{-\frac{L_0}{2}}^{\frac{L_0}{2}}\sqrt{1+\left(\frac{\partial w}{\partial x}\right)^2}\,dx\right) + C_D\mu\left(U - \frac{\partial w}{\partial t}\right)$$

Numerical simulation of the leading order Timoshenko deflection governed by the equation above was solved numerically using a Chebyshev spectral method and a fourth order Runge-Kutta time advancement. The results were found to have good agreement with the low order model.

Furthermore, it can be shown that for the small-angle approximation to be valid, the wire must be in a regime where $\delta \ll L_o$. Collectively, these restrictions can be expressed as conditions on the forcing scale q where $$\frac{Ebh^4}{L_0^4} \ll q \ll \frac{Ebh}{L_0} \qquad\qquad\text{(Eq. 3)}$$

Together, these criteria specify the minimum design criteria to ensure that the governing equations apply to the specific wire geometry and ignore specific material limitations such as yield strength. As N is the tension derived from axial elongation, equation 1 can be expressed as $$-EA\varepsilon\frac{d^2 w}{dx^2} = \left(-\frac{EA}{L_0}\int_{-\frac{L_0}{2}}^{\frac{L_0}{2}} -1 + \sqrt{1+\left(\frac{dw}{dx}\right)^2}\,dx\right)\frac{d^2 w}{dx^2} = q \qquad\text{(Eq. 4)}$$

The small angle approximation can be invoked to simplify the integration through the treatment of w as a second order Taylor approximation. Using the coordinate system outlined in FIG. 1, w can be accurately represented by $w(x) \approx \delta(1-4x^2 L_0^{-2})$. Given that $$\frac{dw}{dx} \ll 1,$$

the integrand in equation 4 can also be simplified as a second order Taylor approximation to give:

$$\frac{-EA}{2L_0}\left(\int_{-\frac{L_0}{2}}^{\frac{L_0}{2}}\left(\frac{\partial w}{\partial x}\right)^2 dx\right)\frac{d^2 w}{dx^2} = q \qquad\text{(Eq. 5)}$$

A closed form solution to this equation can be achieved if a shape of the deflection is assumed. In one embodiment the deflections have been assumed to be small compared to the length, and the shape of the deflected beam can be approximated to leading order by a parabolic curve. Modeling the curve as a parabola facilitates an explicit relationship between a uniform loading and induced strain. A simple integration of a parabolic arc length along the axis of the wire filament reveals that the strain E of the wire filament can be expressed in terms of the L and δ as $$\varepsilon = \frac{8\delta^2}{3L_0^2} \qquad\qquad\text{(Eq. 6)}$$

Integrating equation 5 presents a relationship between the axial stress induced by the strain and the uniform loading, given by $$EA\varepsilon = \frac{qL_0^2}{8\delta} \qquad\qquad\text{(Eq. 7)}$$

This above equation is consistent with a force balance where the external loading must be balanced by vertical component of the force applied at the pinned ends of the wire filament. The midpoint deflection can be solved for explicitly as $$\varepsilon = \frac{1}{2\times 3^{\frac{1}{3}}}\left(\frac{qL}{EA}\right)^{\frac{2}{3}} \qquad\text{(Eq. 8)}$$

and the strain as $$\delta = \left(\frac{3qL_0^4}{64EA}\right)^{\frac{1}{3}} \qquad\text{(Eq. 9)}$$

An important consequence of equations 8 and 9 is that the functional relationship is consistent with the scaling analysis derived from equation 2.

To ensure that the modeling is applicable, q must be related to the fluid flow to determine if the criteria outlined in equation 3. Assuming L is still significantly longer than the deflection scale, δ, the fluid mechanics can be treated as quasi-2D. This assumption allows for the gradients in the fluid flow to be small in the spanwise direction compared to the primary sensing and transverse directions. This implies that the deflection of the beam has a negligible effect on the fluid flow and that the loading on the beam can be related to the local flow velocity around the wire filament. Additionally, if b is sufficiently small so that the Reynolds number based on b, $$Re_b \equiv \frac{\rho \overline{U} b}{\mu} < 50,$$

then the flow can be considered viscously dominated and the drag from the flow can be accurately described using analytic techniques.

In one embodiment of the sensor, the wire filament is configured such that the wire filament in the primary sensing and transverse direction is less than $$\frac{50\mu}{U\rho}$$

throughout a predetermined operating range.

Here, $\rho$ is the fluid density, $\mu$ is the dynamic viscosity of the fluid and $\overline{U}$ is the nominal velocity scale of the flow over the wire. Under these conditions, the local load per unit span, q(x), from the fluid can be describe in a linear fashion as, $$q(x) = C_D U(x) \mu \quad \text{(Eq. 10)}$$

Where U(x) is a velocity component of the flow aligned with the thickness dimension, $\mu$ is the viscosity of the fluid and $C_D$ is the coefficient of drag. While there is no analytic solution for low Reynold's number flow over a 2-d shape, there are several approximations that specify $C_D \approx 1$-10 for slender bodies and cylinders. When $C_D$ is defined in this manner, it should approach a constant value in the limit where $Re_b \rightarrow 0$. However, in one embodiment, the Reynolds numbers were finite and found to be $1 \leq Re_b \leq 10$. In this range, inertial effects become leading order as separation can occur behind the wire filament and $C_D$ is acknowledged to increase with $Re_b$. Collecting the results from equation 9 and 10, the induced strain in flexible wire filament can be directly related to a uniform flow velocity in a closed form manner with $$\varepsilon = \frac{1}{2} \left( \frac{C_D \mu U L_0}{\sqrt{3} \, EA} \right)^{\frac{2}{3}} \quad \text{(Eq. 11)}$$

To evaluate the validity of the result of the above equations, equation 1 with uniform loading was solved numerically for one embodiment and the results were compared to the prediction from the parabolic deflection model. To fully resolve the deflection near the boundary, as the Euler-Bernoulli term can become leading order near the edges, the beam was discretized using a cosine spacing and solved using a Chebyshev spectral method. The equilibrium deflection was found by time advancing equation 17 with a fourth order Runga-Kutta temporal scheme until steady state. The use of a Chebyshev spectral method facilitates a high degree of accuracy and fine resolution near the domain boundaries. Results from simulations with both pinned and fixed boundary conditions were compared to the low order model and were both found to have agreement within a few percent error. The agreement between the numerical solution and the model indicates that the small angle approximation is a valid assumption for wire filaments of this configuration that the Euler Bernoulli term can be assumed to have a negligible impact on the overall deflection of the beam.

Furthermore, with the established relationship between the fluid flow and loading, the validity of the small angle deflection and elastic tension dominated bending can be evaluated. Using the criteria from Eq. 3, a new criteria on velocity can be established for different fluids and wire configurations given by $$\frac{Ebh^4}{C_D \mu L_0^4} \ll U \ll \frac{Ebh}{C_D \mu L_0} \quad \text{(Eq. 12)}$$

Figure 2:
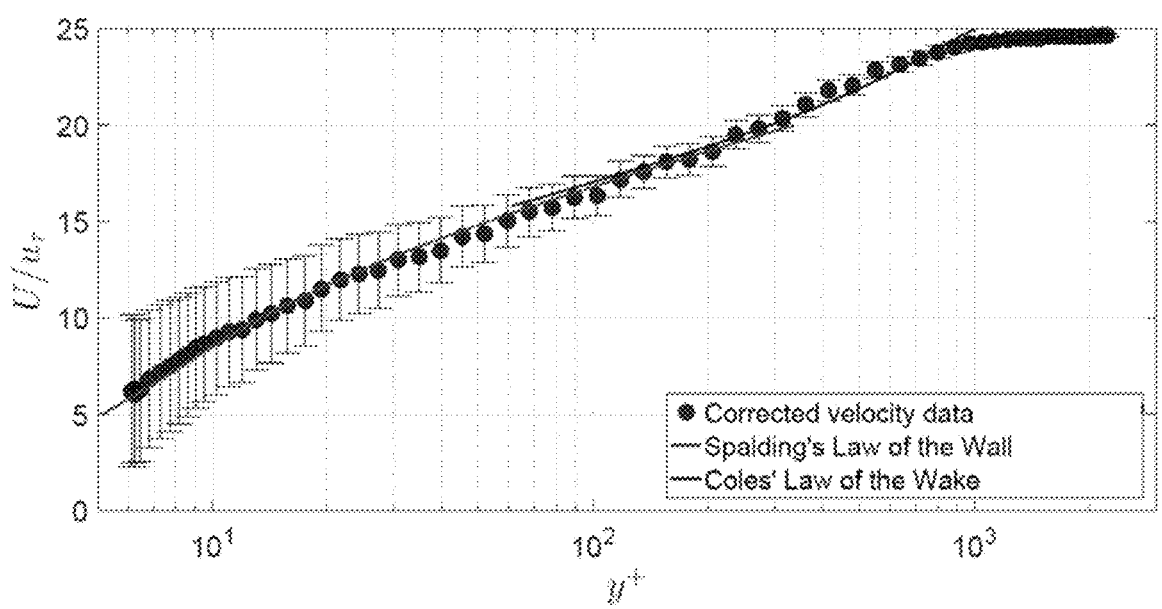
FIG. 2 is a plot of a corrected velocity profile as measured by one embodiment of the present invention.

FIG. 2 provides a plot of a corrected velocity profile of a boundary layer measured by one embodiment of the present invention, plotted in inner coordinates. In FIG. 2, the flow conditions are $Re_\tau = 1218$, with $$Re_\tau = \frac{\rho u_\tau \delta_{99}}{\mu}, u_\tau = \sqrt{\tau_w / \rho},$$

wall shear stress $\tau_w$, fluid density $\rho$, the layer thickness $\delta_{99}$, and dynamic viscosity of the fluid u. FIG. 2 also includes approximate fits for wall and wake regions for comparison. Considering FIG. 2, the criteria from equation 12 can be used to determine the velocity range in which the bending is dominated by elastic tension and captured by the small angle approximation.

In this embodiment, the sensor had $L_0 = 200$ μm, b=2 μm, h=100 nm, E=168 GPa and taking $C_D = 5$, the velocity criteria from inequality 12 is found to be 4 μm/s<<U<<3.3× $10^4$ m/s for water and 200 μm/s<<U<<1.8×$10^6$ m/s for air. It is evident that in both cases the minimum velocity is significantly smaller than many common flow applications of interest and the maximum velocity criteria is significantly larger than any physical flow one could realistically measure. Additionally, the velocities recorded in FIG. 2 are safely within this range. The size of the maximum velocity criteria indicates that it is more appropriately determined through a consideration of the wire yield stress rather than the deviation from the small angle approximation. In one embodiment, a dimension of the wire filament in the primary sensing or transverse direction is less than $$\frac{50\mu}{U\rho}$$

from a velocity of 0 to the velocity at which the stress on the wire in a given fluid exceeds the yield stress of the wire filament. Reassuringly, this result indicates that the small angle approximation should be valid for all velocities of interest, for this particular wire configuration.

With the wire mechanics related to the fluid flow, the classical strain gauge equations can be utilized to relate the strain in the wire filament to a measured resistance change. Through a simple Taylor series approximation it can generally be shown that $$\frac{\Delta R}{R_0} \approx \frac{1}{R_0}\frac{\partial R}{\partial \varepsilon}\bigg|_0 \varepsilon = \left(1 + 2v + \frac{1}{\varrho_0}\frac{\partial \varrho}{\partial \varepsilon}\bigg|_0\right)\varepsilon = GF\varepsilon \quad \text{(Eq. 13)}$$

where R is resistance of the wire defined in the classical manner $R=\varrho LA^{-1}$, $\Delta R$ is the change in resistance from the reference resistance due to strain, v is Poisson's ratio for the wire material, $\varrho$ is the wire resistivity, and the subscript 0 denotes the specific reference state of known temperature and strain. The first two parenthetical terms incorporate the geometric elongation and narrowing derived from strain, while the third is contribution from piezoresistivity. Each of the terms contained in the parenthesis in equation 13 are material properties and independent of wire geometry. It is common to express these terms collectively as a single material specific gauge factor, GF, which relates the fractional change in resistance to the strain. Collecting the results from equations 11 and 13, a functional relationship between the fluid loading and measured resistance is given by:

$$\frac{\Delta R}{R_0} = \frac{GF}{2}\left(\frac{C_D \mu U L_0}{\sqrt{3}\,EA}\right)^{\frac{2}{3}} \quad \text{(Eq. 14)}$$

Here, it is noted that if a single sensor utilizes two or more wires, whereby the sensitivity to temperature and velocity are different between at least two of the wires, one will be able to differentiate between changes in temperature and strain. Preferably, in a sensor comprising two or more wires, the first wire filament has a different stiffness or physical dimension, or otherwise has a different sensitivity to at least one of velocity or temperature than the second wire filament.

Though the relations used to derive equation 14 neglected the effects of pre-stress or pre-deformation, equation 7 can be modified to include these effects and a more complicated approximation for the strain can be derived.

Closure of the nonlinear, steady-state deflection equation with a parabolic shape profile neglected the effects of finite tension or compression in the unloaded wire filament. A simple modification to equation 7 yields the new equation $$EA\varepsilon - \sigma_0 = \frac{qL_0^2}{8\delta} \quad \text{(Eq. 18)}$$

where $\sigma_0$ is the pre-existing axial stress in the unloaded wire filament. A negative $\sigma_0$ corresponds to a pre-tension, while a positive $\sigma_0$ will be treated as an equivalent deflection of the wire in the unloaded state. Combining equations 18 and 6 gives a modified equation for the deflection $$q^+ = \frac{3qL_0}{EA}$$

$$\sigma_0^+ = \frac{2\sqrt[3]{4}\,\sigma_0}{E}$$

$$\delta = \frac{\sqrt[3]{4}\,L_0}{8}\left(\sigma_0^+\left(q^+ + \sqrt{(q^+)^2 - (\sigma_0^+)^3}\right)^{-\frac{1}{3}} + \left(q^+ + \sqrt{(q^+)^2 - (\sigma_0^+)^3}\right)^{\frac{1}{3}}\right)$$

It is clear that when $\sigma_0 \to 0$, the relationships revert to the results in equations 8 and 9. The overall effect of both pre-tension and pre-deflection is to reduce the net change in deflection and strain experienced by the wire under load.

It can be shown that the net effect of both of these effects is to depress the change in strain from the external loading. Furthermore, if the pre-stress is small compared to the fluid loading, then the effects on the mechanics are negligible.

With the functional relationship between fluid load and the wire resistance established in equation 14, it is preferred that the wire filament have high gauge factor GF, low Young's modulus E, large span $L_0$, and small cross sectional area A. In other words, for a given fluid flow, a long and thin wire will be more sensitive; a carefully chosen material with low E and high GF will further boost the sensitivity. To ensure the fluid forcing is in the viscously dominated regime, base of the wire, b, needs to be small, preferably on the order of micrometers. In a preferred embodiment, the base is less than 200 micrometers. In a more preferred embodiment, the base is less than 100 micrometers. In an even more preferred embodiment, the base is less than 50 micrometers. In a still more preferred embodiment, the base is between 0.1 and 10 micrometers.

Many materials can provide the necessary functionality. In one embodiment, the wire filament comprises at least one of: a pure metal (e.g., platinum or gold, etc.) or a metal alloy (e.g., platinum-copper, gold-palladium, nichrome, etc.), an electrically conductive polymer, or a piezoresistive material. Preferably, platinum (Pt) stands out as one good candidate with high piezoresistivity, high ductility, low thermal expansion coefficient. Platinum has a moderate Young's modulus among metals, but is nonreactive and easy to process using standard MEMS techniques to form thin films. Further, as a noble metal, no oxidation layer will form to complicate the process. Additionally, materials with low TCR are preferred. In some cases, however, it may be beneficial to incorporate more than one material, including but not limited to a metal and a dielectric material, an alloy or lamination of metallic materials, a non-conductive polymer and a conductive polymer, or a biologic and a piezoresistive material.

Because these sensors can be utilized in a variety of environments, many different factors need to be taken into account when designing an appropriate sensor—choice of material or materials, wire dimensions, orientation, chip packaging, and more all come into play. For example, a device designed to measure the speed of a car will necessarily have a different operating range of velocities and environmental factors (e.g., 0-120 mph in air between $-50°$ C. and $50°$ C.) than one designed for a boat (e.g., 0-40 mph in salt water between $0°$ C. and $40°$ C.). And both would be different from a sensor designed for measuring velocities in a large-duct air handling systems (0-20 mph in air between $15°$ C. and $50°$ C.) or one for measuring sewage flow underground, measuring the velocity of a flammable gas in an industrial setting, or measuring the flow of blood through a tube in a hospital. In some environments, the need to be able to clean, sanitize and/or sterilize the sensor may also be necessary. For example, if the sensor is used as a flowmeter in the pharmaceutical industry, it could be required to compatible with clean-in-place (CIP) and/or sanitize-in-place (SIP) capabilities of the facility, and certain configurational changes would be required to enable such compatibility.

Example Apparatus

Pipe flow is one of the simplest flows to study and its velocity profile is well understood across a wide range of Reynolds numbers. In one exemplary apparatus, the sensor is designed to interface directly with a pipe by having a 4 mm through-hole at the center, which is spanned by the sensing wire filament. The span-to-base ratio of the free-standing wire filament is limited by the strength of the metal thin film and was kept under 150 to maintain the integrity of the wire during processing in this example. Minimal supporting structures were deployed to hold the wire filament to minimize blockage effects that could alter the flow in the vicinity of the sensing element.

Figure 9:
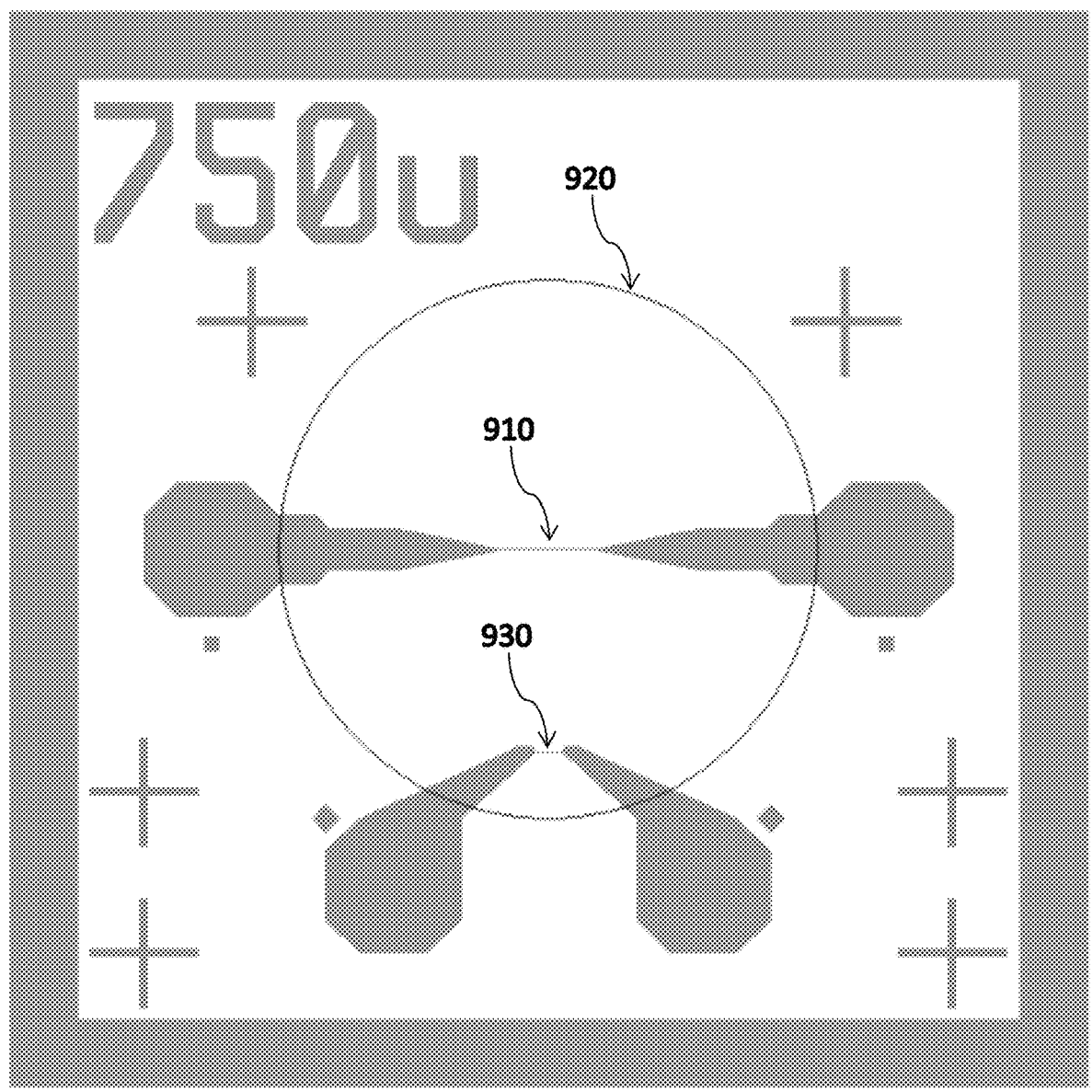
FIG. 9 is a front side mask of one embodiment of the present invention.

A compact layout of an exemplary chip is shown in FIG. 9, where the sensing wire (910) has a dimension of 750×6.5 µm. The black circle shows the position of the 4 mm hole (920), although such a hole is not required in other embodiments, provided the wire filament can be exposed to fluid flow, and the area colored in red will be deposited with platinum. In this example, the 8×8 mm chip is designed to be mounted to a larger printed circuit board (PCB) with the same sized through-hole and electrical leads for taking measurements.

One main disadvantage of platinum is its moderate temperature coefficient, meaning its resistance can easily be influenced by ambient temperature. Because platinum has a near-constant temperature coefficient for a large range of temperature, this property has been commonly used for sensors such as hot- and cold-wires. To decompose the contributions of velocity and temperature towards the change in resistance, a second wire (930) of dimension 200×2.5 µm was added to the sensor for accurate temperature measurement, which allows velocity signal to be decoupled from temperature change.

The manufacturing of this chip utilizes standard semiconductor and MEMS techniques. Starting with a polished 100 mm silicon wafer, a 500 nm layer of silicon nitride is deposited at 250° C. using plasma-enhanced chemical vapor deposition (PECVD). This layer of silicon nitride acts as an electrical insulating layer between the platinum layer and silicon wafer. About 40 chips shown in FIG. 9 were patterned onto the silicon nitride side of the wafer using standard bilayer-resist photolithography to allow clean edges of the features after metal lift-off. 150 nm of platinum is then sputtered onto the pattern with 10 nm of titanium (Ti) underneath to aid adhesion to silicon nitride.

Figure 10:
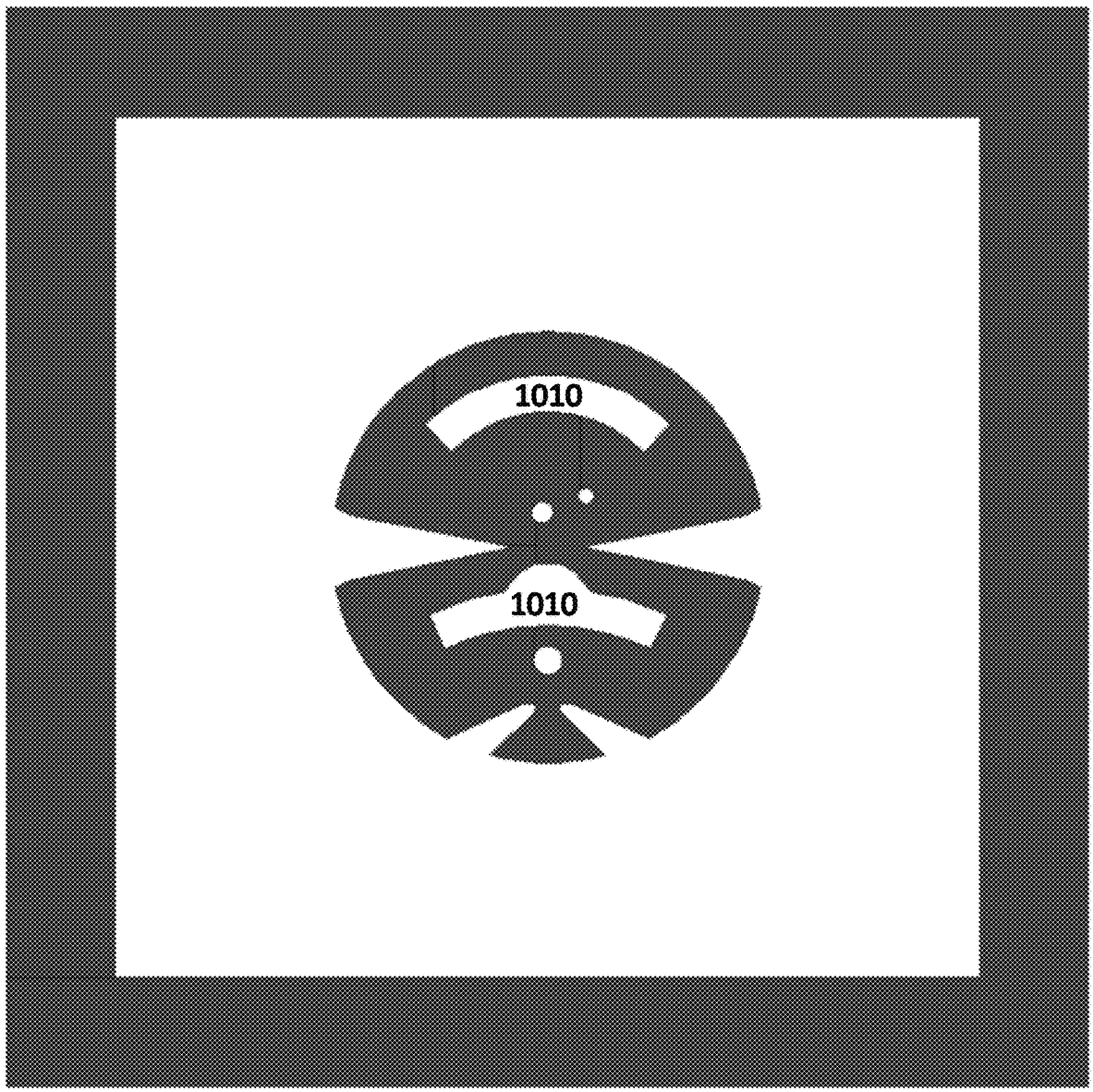
FIG. 10 is a back side mask of one embodiment of the present invention.

To create the through-hole for pipe flow experiment, deep reactive-ion etching (DRIE) is used to etch the wafer from the backside (non-metal side). DRIE is a highly anisotropic etch process used to create high aspect ratio features with straight walls by alternating between etcher and protecting gas plasmas that are driven toward the wafer with a generated electric field. A mask is designed to create the through-hole and at the same time, release individual chips from the 100 mm silicon wafer. One example of such a mask is the 10×10 mm mask shown as FIG. 10. This process avoids the use of a dicing saw where the generated debris can be destructive to the free-standing features. Because the blockage of the through-hole is designed to be small, there are relatively few structures to support the silicon being etched away. As the etched silicon becomes very thin, it can easily propagate cracks that break the wires. To prevent this from happening, obstructive "islands" (1010) are added to create barriers and divide the hole into smaller areas. In each divided areas, the center tends to etch slightly faster, making it the first point to etch through. Different lattice spacing and elevated temperature during nitride deposition is responsible for a residual stress at the silicon wafer and silicon nitride interface. When the wafer is etched through, the silicon will release energy and rupture around the first point of opening. Since the platinum wire filament is only 150 nm in thickness, a rupture would most likely cause the wire to break and render the sensing element unusable. Therefore, obstructive "islands" introduced are placed in an asymmetric fashion (1010), promoting the rupture to occur away from the wire. The introduction of asymmetric "islands" during through-hole etching proved to significantly increase the yield of the sensor manufacturing process.

Figure 11:
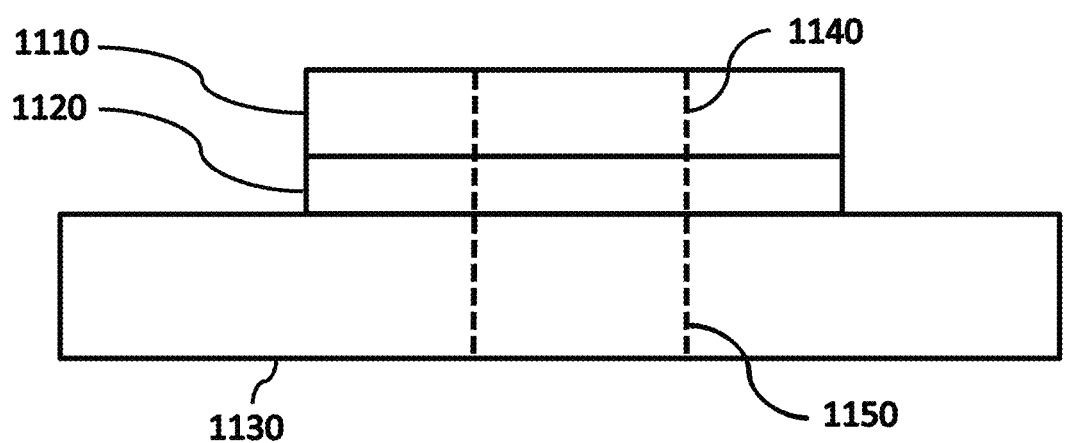
FIG. 11 is a block diagram of one embodiment of a sensor chip mounted on a substrate.

Once the chips are released from the wafer, another silicon dry etch with sulfur hexafluoride is performed to clean up excess silicon in the through-hole and remove the PECVD silicon nitride. As shown in FIG. 11, the chip (1110) is then mounted to a PCB (113), optionally using a bonding agent (1120), such as conductive epoxy for good electrical connections. Optionally, a metallurgic connection, such as the use of solder balls, could also be used instead of a bonding agent. In this example, the through-hole in the chip (1140) was aligned with the hole in the hole in the PCB (1150) when the chip was mounted. Although this illustration shows a mounted chip, the chip could also be embedded in the PCB or other substrate, given appropriate alignment of the various holes, or it could be mounted on other structures. The device could also incorporate a housing (not shown) that would prevent most of the electronic circuitry from being exposed to the environment, leaving as little as the wire filament itself exposed.

Preferably, the sensor will incorporate a circuit for measuring voltages or resistances, such as through a Wheatstone bridge, although those skilled in the art will recognize that there are other techniques that could be used. Using techniques known in the semiconductor and integrated circuit industry, the PCB may also optionally include one or more active and/or passive components, such as a processor, memory, or a wireless transceiver, or may provide connections for a keyboard, mouse, display, or other user interface. The processor may be configured to receive a signal comprising the voltage or resistance of the wire filament and output a signal comprising a calculated fluid stream velocity, preferably based on a previously stored calibration curve. The wire filament voltage or resistance, or the calculated fluid stream velocity, can then be displayed on a user interface, can be transmitted in a wired or wireless fashion to a remote computer or server, or otherwise communicated to another device or to a user.

Preferably, the sensor will also incorporate a circuit configured to automatically adjust the output for temperature changes or current changes. This can be done passively in the Wheatstone bridge or it could involve a feedback loop, using a circuit for measuring voltages or resistances in conjunction with a circuit for controlling current through the wire filament. If two or more wire filaments are utilized, each can have its own control circuitry.

Figure 12:
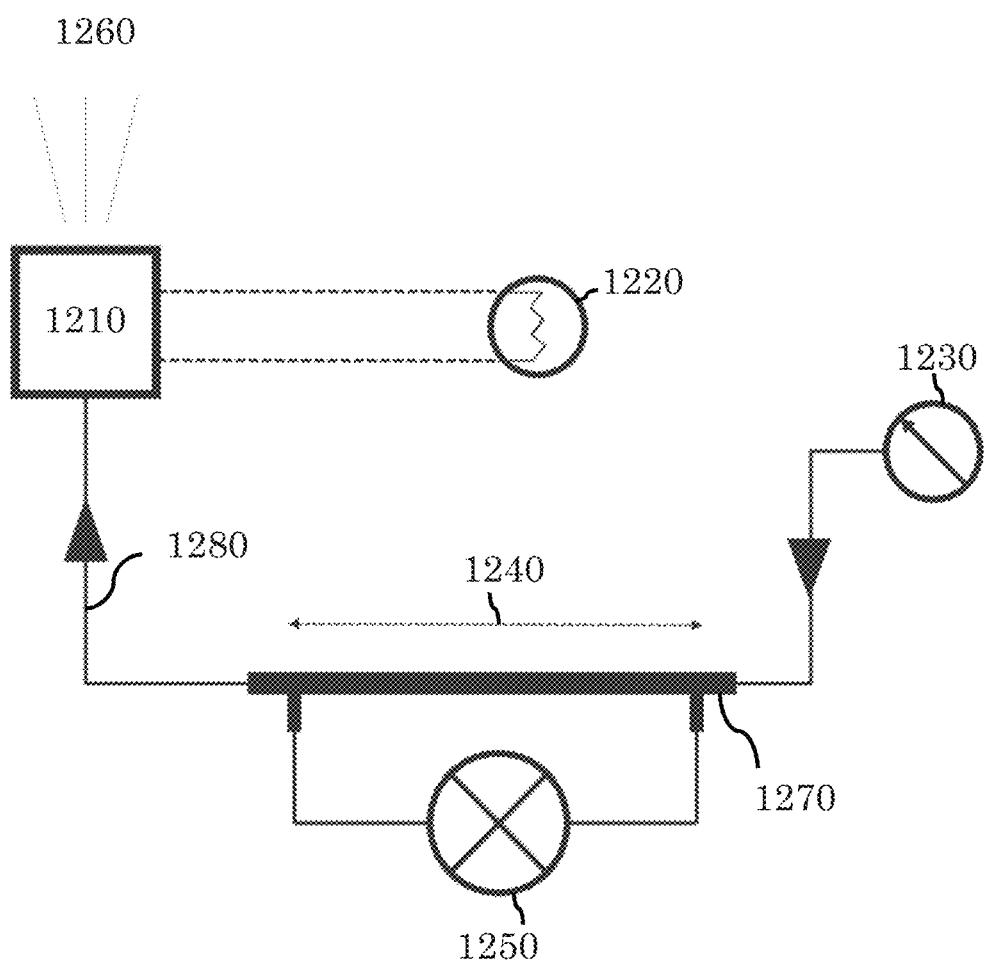
FIG. 12 is a diagram of a test setup for analyzing performance of the present invention.

In one example, the sensor was evaluated using the setup shown in FIG. 12, which was configured to use either water or air as the working fluid. Fluid flow controlled by a pressure regulator (1230) was directed through a section of calibrated smooth pipe (1270). Bulk flow velocity was determined by measuring the pressure drop using a pressure transducer (1250) over a length (1240), 1, where the flow was fully developed. Flow exiting the tube (1280) would pass over the wire in the sensor (1210), inducing a strain and resistance change before the flow exits the system (1260). The fractional resistance changes were measured by integrating the wire as part of a Wheatstone bridge (1220). The voltage across the bridge was directly related to the resistance change in the wire through the known values of the bridge circuit components.

Figure 3:
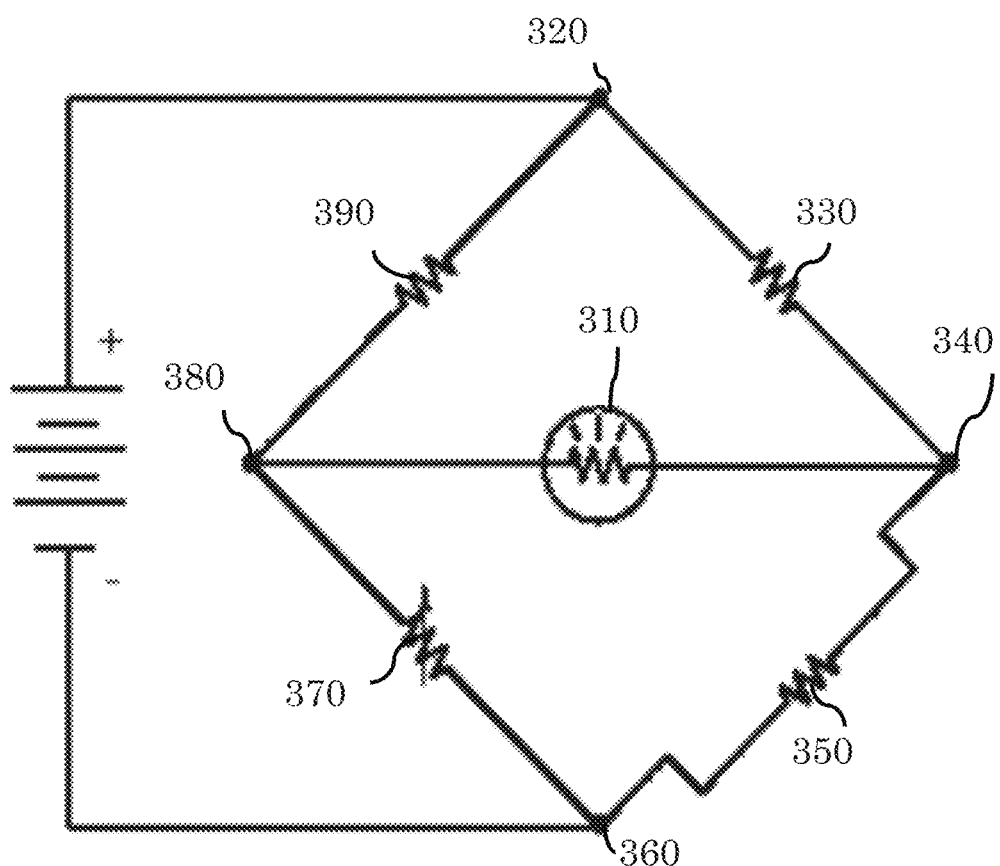
FIG. 3 is a diagram of a Wheatstone bridge.

FIG. 3 shows a sample Wheatstone bridge. In one exemplary method, the voltage relates the resistances in the following manner:

$$V_G = \left( \frac{R_2}{R_1 + R_2} - \frac{R_x}{R_x + R_3} \right) V_s$$

Where $R_1$, $R_3$ (390, 330) are large but known resistors, $R_2$ (370) is a tunable resistor close to the resistance of the wire filament, $V_G$ (310) denotes measured potential difference between points B (340) and D (380), $V_S$ denotes measured potential difference between points A (320) and C (360), and $R_X$ denotes the resistance of the first wire filament (910). One can optionally replace $R_2$ (370) with a second wire filament (930) exposed to substantially the same fluid flow as the first wire filament, but with a different configuration such that it has different performance characteristics (for example, reduced or increased sensitivity to velocity or temperature).

In this example, each of these components in the bridge were carefully chosen to minimize the resistive heating in the wire, while ensuring a measurable level of sensitivity to flow loading: current in the Wheatstone bridge was limited to 67 μA, which means less than 1% of measured resistance change is due to Joule heating if wire is under water; however, Joule heating will contribute more in air, especially at lower velocities. In experiments conducted with confocal microscopy, the objective lens was placed above the outlet of the system in line with the flow (1260).

Figure 8:
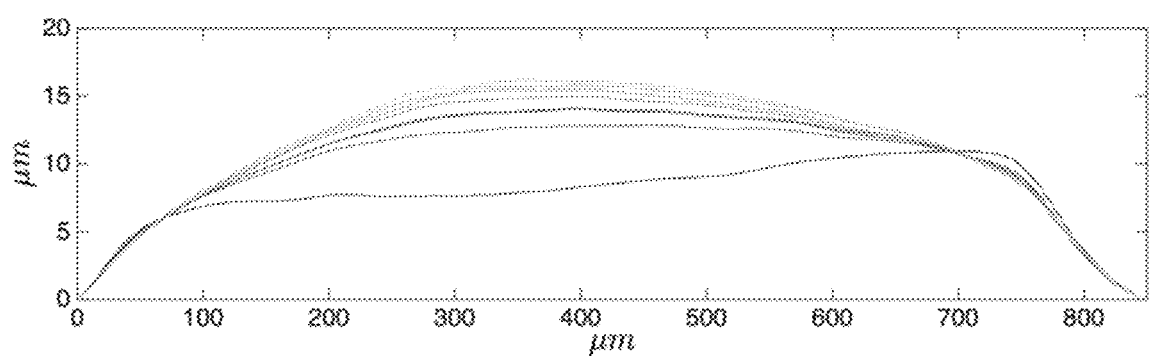
FIG. 8 is a centered linear thickness profile of one embodiment of a wire filament.
Figure 13:
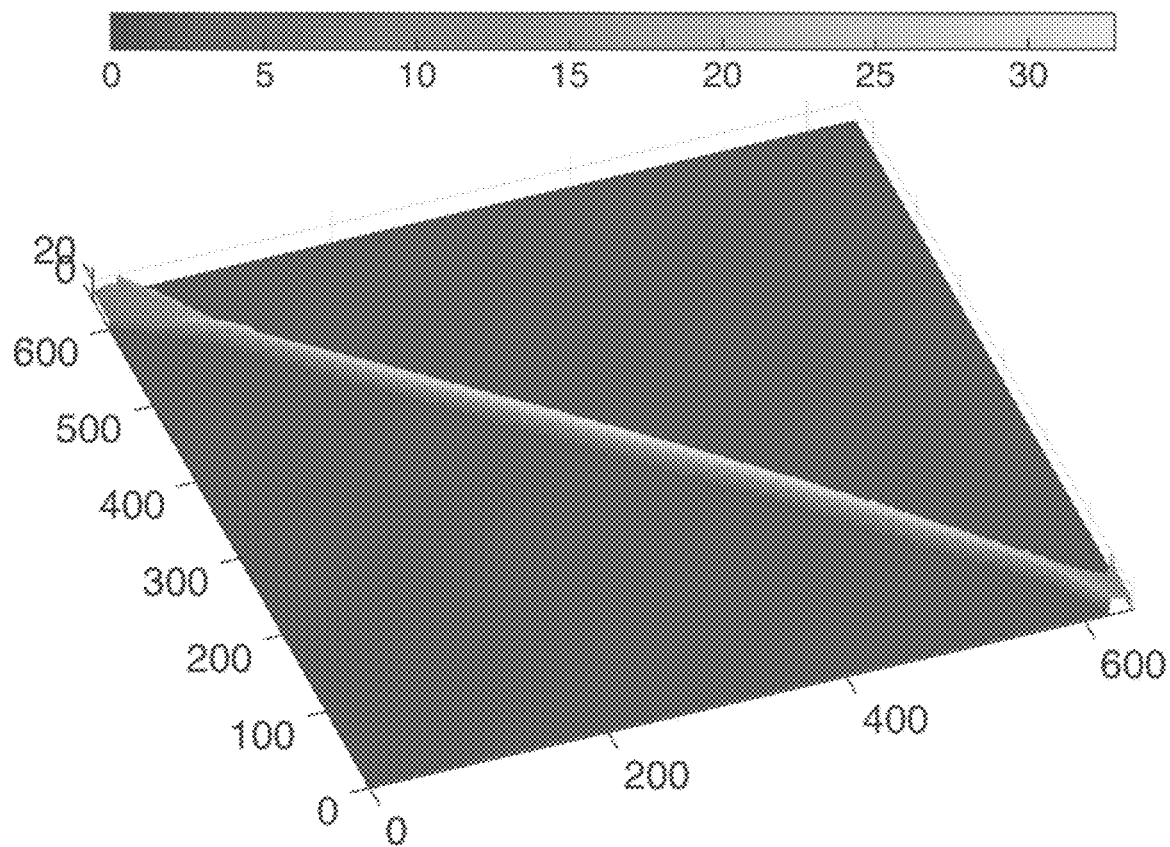
FIG. 13 is a confocal image of one embodiment of a wire filament in air.

As shown in FIG. 13, confocal imaging of a 750 μm by 6.5 μm by 150 nm sensor was performed while the wire was exposed to bulk flow velocities up to 20 m/s to further investigate and validate the modeling. Two-dimensional area maps of the wire filament deflection, see FIG. 13, were recorded for several different flow velocities of nitrogen. From each area map, a centered linear thickness profile of the wire filament was extracted, as seen in FIG. 8. Numerical integration was performed along the length of each profile to find the elongation due to the flow, shown as FIG. 5.

It is noted that from FIG. 8, the profile of the unloaded wire filament indicates a pre-existing, asymmetric deformation. As the wire filament is loaded while in flow, the shape of the deflection adheres more closely to the expected parabolic curve and that there is an increasing deformation compared to the unloaded configuration. The remaining deviation from a symmetric, parabolic shape can be best explained by the presence of two triangular platinum support that are partially free-standing as well. The relative size and shape of the deflections validate that the parabolic shape and small angle approximations are appropriate for the wire mechanics. Furthermore, the relative size of the deflection compared to the thickness implies that the force balance is dominated by the elastic elongation rather than flexural rigidity.

The strain resulted from the microscopy are compared to the theoretical prediction for ε from equation 11. Given that $C_D$ is known to increase with Reynolds number, a functional relationship between Re and $C_D$ is necessary to determine the fluid forcing. To approximate this trend, an empirical relation of Re and $C_D$ for a cylinder of diameter b is applied.

$$C_D \approx 0.59 \text{Re}_b + 3.4 \text{Re}_b^{0.11} + 0.98 \text{Re}_b^{0.5} - \frac{0.0002 \text{Re}_b^2}{1 + 3.64 \times 10^{-7} \text{Re}_b^2} \quad \text{(Eq. 15)}$$

Though there is no expectation that $C_D$ of a cylinder should match that of a bluff ribbon, this estimate should capture the overall magnitude and trend of the drag over the span of Reynolds numbers considered in this example.

Figure 5:
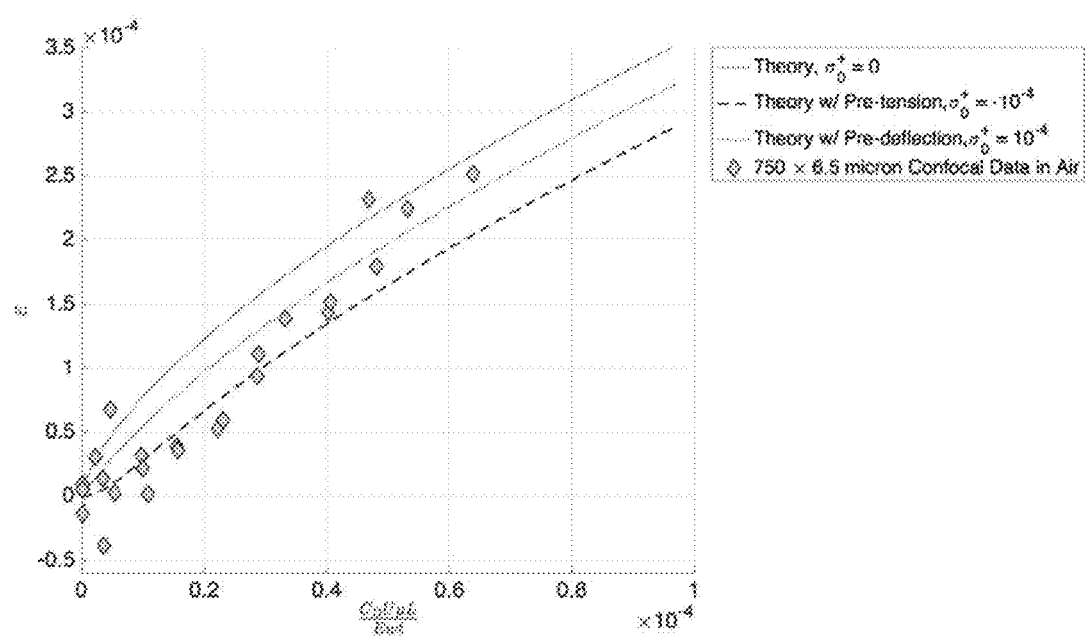
FIGS. 5-7 are plots of measured results of embodiments of the sensor versus theoretical predictions.

FIG. 5 shows the comparison between the measured strain and the predictions from the model for the approximate fluid loading. Despite the uncertainty in $C_D$, there is a reasonable agreement between the slopes predicted by the model and the experimental results. Though the results deviate from the simplest form of the model, where pre-stress and pre-deflection are neglected, when these results are factored.

Figure 6:
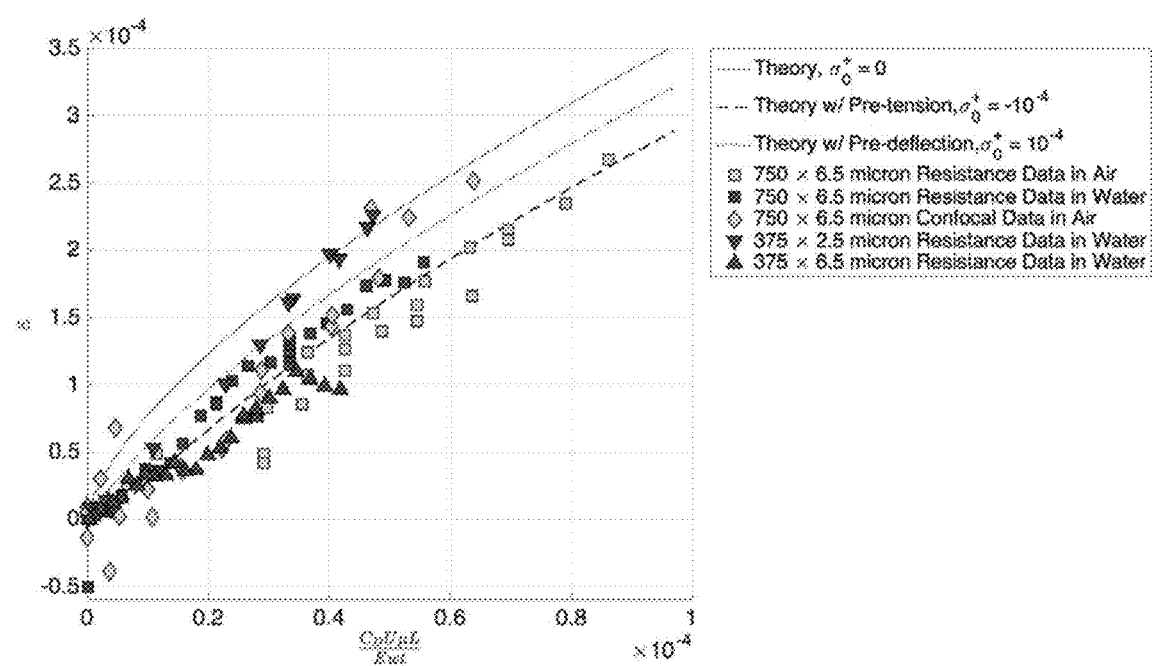

Embodiments of these sensors are able to accurately capture the scaling theory, as seen in FIG. 6. Several embodiments were tested in water (dark symbols) and in air (lighter symbols), each embodiment having various dimensions, and the results are compared against the theoretical curves. FIG. 6 shows the resistance change calculated from voltage measurements while under load. $C_D$ is approximated with that of a cylinder with diameter b for this flow regime and GF approximated as 2.4 for platinum. Wire sizes in this example included 750×6.5 μm (squares), 750×6.5 μm with confocal imaging (diamonds), 375×6.5 μm (point-up triangles), and 375×2.5 μm (point-down triangles).

One immediately noticeable trend is the sensitivity vs. wire size is consistent with the theoretical prediction. In FIG. 6, the least sensitive wire ended up being the 375×6.5 μm geometry, while the most sensitive was the 750×6.5 μm geometry. These results are expected, as a longer wire is exposed to more forcing, while a wider wire has a higher resistance to bending.

Figure 7:
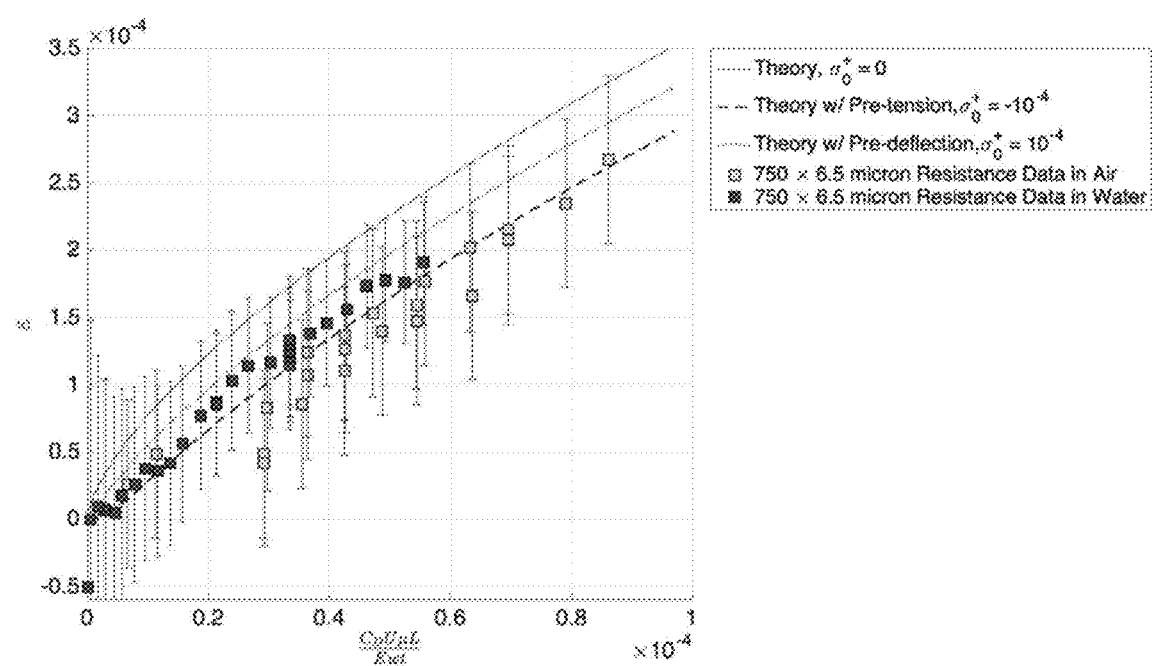

A more detailed analysis of a single wire is shown in FIG. 7, which compares the 750×6.5 μm wire with the theory. The additional theory lines include the factor $\sigma_0^+$ to account for any pre-tension or pre-deflections in the wire due to the manufacturing process. The exact magnitude of the pre-tension or compression in the experimental setups are not known, but a range of possible values are illustrated in the two figures.

Additionally, the error bars included are representative of the uncertainty of the temperature of the fluid at the wire. For the measurements taken with water, the small temperature difference between the walls of the pipe and the bulk flow would lead to a drift in temperature for different velocities. The temperature measurement location does not coincide with the wire filament, but is actually displaced downstream by a few mm, leading to an uncertainty in the actual temperature of the filament. Additional uncertainty lies in the temperature calibration of the filament itself. In one embodiment, a shift of 0.005° C. in the calibration offset results in a change in Δ R/R by up to 0.0002.

This temperature drift of the system can be seen in the error bars of FIG. 7, noting that the error increases with decreasing fluid forcing. As the flow rate decreases, the heat transfer from the water to the piping in the system becomes more pronounced, causing the temperature of the fluid to fall. Since the higher flow rates will have a higher temperature (due to the water reservoir being slightly higher temperature than the system), an artificially higher voltage will be recorded. This temperature drift is approximately accounted for with the thermocouple, but the finite distance between the thermocouple and filament result in a different temperature measured than felt by the wire. The faster velocities result in a more accurate temperature measurement, since there is less temperature drop between the filament and thermocouple.

In the case of the data taken in air, the temperature has an uncertainty due to the small calibration offset and the variance of the measurement itself. This leads to a very similar error bar across all measurements, compared to the increasing error with decreasing velocity in water.

Some uncertainty lies in the precise value for $C_D$ over the wire. As the flow velocity increases, the $C_D$ will increase.

The error bars only contain the two temperature contributions, indicating that a precise measurement of the filament temperature is paramount to improving the accuracy of the sensor given a specific wire filament material choice. Alternatively, a material with a lower TCR can be utilized. A second wire exposed to the flow but fixed to prevent any deflection would allow a very accurate temperature measurement in close proximity to the filament, enabling precise temperature calibration of the sensor itself.

Figure 4:
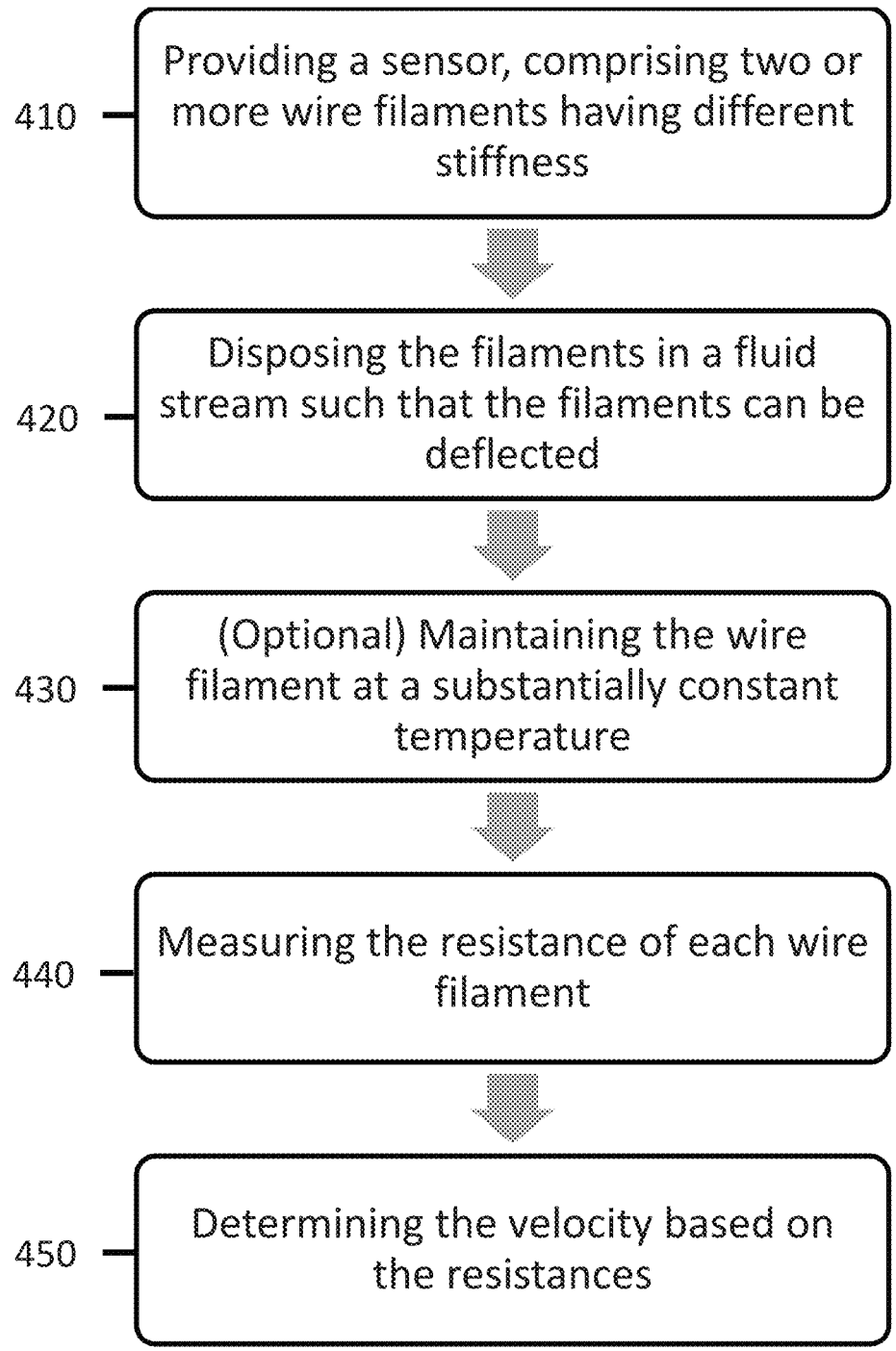
FIG. 4 is a flowchart of one embodiment of a method for measuring velocity.

The flowchart of one exemplary method for determining velocity of a fluid stream is depicted in FIG. 4. The method first requires providing a sensor comprising two or more wire filaments, each having a different stiffness (410). The wire filaments are then disposed in a fluid stream, such that the filaments can be deflected (420). Optionally, each wire filament is maintained at a substantially constant temperature (430). It is believed that the two filaments do not have to be maintained at the same temperature. Using a measuring circuit, such as a Wheatstone bridge, the resistance of each of the two wire filaments is measured (440). The velocity of the fluid stream can then be equated to the result of a function of the two resistances (450). Preferably, at least one of the wire filaments has a length dimension longer than at least one of a width or thickness dimension and is capable of being deflected when exposed to the fluid stream. At least one wire filaments should have a dimension in the primary sensing or transverse direction of less than $$\frac{50\mu}{U\rho},$$

throughout a predetermined design or operating range, where μ is viscosity of the fluid stream, ρ is density of the fluid stream, and U is velocity of the fluid stream relative to the wire filament.

Various modifications and variations of the invention in addition to those shown and described herein will be apparent to those skilled in the art without departing from the scope and spirit of the invention, and fall within the scope of the claims. Although the invention has been described in connection with specific preferred embodiments, it should be understood that the invention as claimed should not be unduly limited to such specific embodiments.

What is claimed is:

1. A velocity sensor system configured to measure velocity of a fluid stream, the sensor system comprising two or more electrically conductive wire filaments, wherein the two or more electrically conductive wire filaments are configured to have a length dimension longer than at least one of a width or thickness dimension,
   wherein at least one of the two or more electrically conductive wire filaments is adapted to be deflected when exposed to the fluid stream,
   wherein, for the at least one of the two or more electrically conductive wire filaments, a dimension in at least one of the width or thickness is less than $50\mu/U_p$ throughout a predetermined operating range of expected fluid velocities,
   where μ is viscosity of the fluid stream, ρ is density of the fluid stream, and U is velocity of the fluid stream relative to the at least one of the two or more electrically conductive wire filaments, and wherein the velocity of the fluid is related to a change in voltage or resistance across the at least one of the two or more electrically conductive wire filaments due to strain.

2. The velocity sensor system according to claim 1, wherein at least one of the two or more electrically conductive wire filaments is supported at both ends.

3. The velocity sensor system according to claim 1, wherein at least one of the two or more electrically conductive wire filaments is freestanding.

4. The velocity sensor system according to claim 1, wherein at least two of the electrically conductive wire filaments are connected in series.

5. The velocity sensor system according to claim 1, wherein at least two of the electrically conductive wire filaments are connected in parallel.

6. The velocity sensor system according to claim 1, wherein the length of at least one of the two or more electrically conductive wire filaments is between and including 10 and 100,000 times that of both the primary sensing and transverse dimensions.

7. The velocity sensor system according to claim 1, wherein at least one wire filament comprises material with a Young's modulus between and including 0.001 and 500 GPa, and a yield strength between and including 30 and 3,000 MPa.

8. The velocity sensor system according to claim 1, wherein the thickness of the at least one of the two or more electrically conductive wire filaments is less than $$L\left(\frac{\mu U}{Ew}\right)^{\frac{1}{4}},$$

throughout a predetermined operating range of expected fluid velocities, where μ is viscosity of the fluid stream, E is the Young's modulus of the wire filament, w is the dimension in the transverse direction, L is the filament length of the sensor of claim 1, and U is velocity of the fluid stream relative to the wire.

9. The velocity sensor system according to claim 1, wherein at least one of the two or more electrically conductive wire filaments comprises a material that experiences a change in its resistance when deformed.

10. The velocity sensor system according to claim 1, wherein at least one of the two or more electrically conductive wire filaments comprises at least one of: a pure metal or a metal alloy, an electrically conductive polymer, a semiconductor material or a piezoresistive material.

11. The velocity sensor system according to claim 1, wherein at least one of the two or more electrically conductive wire filaments comprises two or more materials.

12. The velocity sensor system according to claim 1, wherein at least two of the electrically conductive wire filaments have a different sensitivity to temperature.

13. The velocity sensor system according to claim 1, further comprising a circuit configured to measure a voltage or resistance of at least one of the two or more electrically conductive wire filaments.

14. The velocity sensor system according to claim 1, further comprising a circuit configured to measure the differential between the voltage over the wire filaments configured to deflect when exposed to a flow, and the voltage over the filaments configured to not deflect.

15. The velocity sensor system according to claim 14, further comprising a sensor housing adapted to protect at least the circuit.

16. The velocity sensor system according to claim 1, further comprising:
a circuit configured to automatically adjust output based on temperature.

17. The velocity sensor system according to claim 16, further comprising a sensor housing adapted to protect at least the circuit.

18. The velocity sensor system according to claim 1, further comprising a processor adapted to receive a signal comprising the voltage or resistance of the wire filament and output a signal comprising a calculated fluid stream velocity.

19. The velocity sensor system according to claim 1, further comprising a wireless transceiver capable of transmitting a signal comprising at least one of: the voltage of at least one of the two or more electrically conductive wire filaments, the resistance of at least one of the two or more electrically conductive wire filaments, or a calculated fluid stream velocity.

20. A method for determining velocity of a fluid stream, comprising the steps of: providing two or more wire filaments, where at least one of the two or more wire filaments is adapted to be deflected when exposed to the fluid stream;
measuring a resistance of each of the at least two of the two or more wire filaments; and
equating the velocity of the fluid stream to the result of a function of the at least two resistances,
wherein at least one of the two or more wire filaments has a length dimension longer than at least one of a width or thickness dimension, and at least one of the two or more wire filaments has a dimension in at least one of width or thickness less than $50\mu/U_p$ throughout a predetermined operating range, where $\mu$ is viscosity of the fluid stream, $\rho$ is density of the fluid stream, and U is velocity of the fluid stream relative to the one of the two or more wire filaments, and
wherein the velocity of the fluid is related to the strain of the at least one of the two or more wire filaments.

* * * * *